(12) United States Patent
Benedict

(10) Patent No.: US 9,820,785 B2
(45) Date of Patent: Nov. 21, 2017

(54) BONE AFFIXING APPARATUS AND METHOD FOR USING THEREOF

(71) Applicant: Yeshaiau Benedict, Moshav Benaya (IL)

(72) Inventor: Yeshaiau Benedict, Moshav Benaya (IL)

( * ) Notice: Subject to any disclaimer, the term of this patent is extended or adjusted under 35 U.S.C. 154(b) by 158 days.

(21) Appl. No.: 14/534,230

(22) Filed: Nov. 6, 2014

(65) Prior Publication Data

US 2015/0133937 A1    May 14, 2015

(30) Foreign Application Priority Data

Nov. 14, 2013  (IL) .......................................... 229435

(51) Int. Cl.
*A61B 17/56* (2006.01)
*A61B 17/72* (2006.01)

(52) U.S. Cl.
CPC .............................. *A61B 17/7258* (2013.01)

(58) Field of Classification Search
CPC .................. A61B 17/7002–17/7031; A61B 17/72–17/7291; A61B 17/68
See application file for complete search history.

(56) References Cited

U.S. PATENT DOCUMENTS

| | | |
|---|---|---|
| 3,269,251 A | 8/1966 | Bass |
| 5,141,435 A | 8/1992 | Lillard |
| 5,702,215 A * | 12/1997 | Li ........................ F16B 13/0866 411/21 |
| 8,486,120 B2 | 7/2013 | Shimko |
| 2005/0159749 A1* | 7/2005 | Levy ...................... A61B 17/68 606/62 |
| 2006/0036248 A1* | 2/2006 | Ferrante ............. A61B 17/7225 606/64 |
| 2006/0229617 A1* | 10/2006 | Meller ................. A61B 17/746 606/62 |
| 2008/0161805 A1* | 7/2008 | Saravia .............. A61B 17/1725 606/60 |
| 2011/0077651 A1* | 3/2011 | Lozier ................ A61B 17/7258 606/62 |
| 2011/0137312 A1* | 6/2011 | Mantovani ......... A61B 17/7233 606/63 |
| 2012/0270181 A1 | 10/2012 | Shribman |
| 2013/0123857 A1 | 5/2013 | Biedermann |
| 2013/0274747 A1* | 10/2013 | Fagan ................ A61B 17/7225 606/64 |

* cited by examiner

*Primary Examiner* — Ellen C Hammond
*Assistant Examiner* — Tessa Matthews
(74) *Attorney, Agent, or Firm* — Daniel J. Swirsky; AlphaPatent Associates Ltd.

(57) ABSTRACT

A bone affixing apparatus including a substantially hollowed shaft for being inserted into the bone, at least one projectable element disposed within the shaft, and a first mechanism for projecting prongs of the at least one projectable element out of shaft into a tissue of the bone, thereby eliminating breaching the bone from the outside of the bone.

7 Claims, 11 Drawing Sheets

BONE AFFIXING APPARATUS AND METHOD FOR USING THEREOF

CROSS-REFERENCE TO RELATED APPLICATIONS

This application claims priority from Israel Patent Application No. IL 229,435, filed Nov. 14, 2013, the contents of which are incorporated herein by reference in their entirety.

TECHNICAL FIELD

The invention relates to the field of bone healing. More particularly, the invention relates to an apparatus and method therefore.

BACKGROUND

Bone healing, or fracture healing, is a proliferate physiological process in which the body facilitates the repair of a bone fracture. Generally, bone fracture treatment consists of a doctor reducing (pushing) displaced bone fragments back into place via reduction, with or without anesthetic, stabilizing their position, and then waiting for the bone's natural healing process to occur.

The process conventionally applies inserting a rod within a bone, and then threading prongs, nails or screws into the bone and into the rod, for affixing the rod to the bone.

However, the prongs, nails or screws must enter the pre-determined locations of the rod, being hidden.

All the methods described above have not yet provided satisfactory solutions to the problem that the rod is hidden.

X-ray imaging is not a satisfactory solution, since in contrast to video, it does not provide real time images.

SUMMARY

A method and apparatus is provided for affixing a rod to a bone such that the hidden state of the rod does not reduce the quality of the affixing.

In one aspect, the invention is directed to a bone affixing apparatus having:
- a substantially hollowed shaft, for being inserted into the bone;
- at least one projectable element, disposed within the shaft; and
- a first mechanism, for projecting prongs of the at least one projectable element out of shaft into a tissue of the bone,
- thereby eliminating breaching the bone from the outside of the bone.

The at least one projectable element may include at least two projectable elements, each disposed at a different longitudinal location of the bone.

The bone affixing apparatus may further include:
- a second mechanism, for drawing the at least two projectable elements one towards the other after the projection thereof,
- thereby allowing drawing two fragments of the bone one towards the other.

The at least one projectable element may include a lever being pivotally connected to the hollowed shaft, thereby linear motion of a margin of the lever presses the prongs.

The first mechanism for projecting the at least one projectable element out of shaft into a tissue of the bone may include a screw, for moving linearly upon rotation thereof, for pushing a lever projecting the at least one projectable element.

The first mechanism for projecting the at least one projectable element out of shaft into a tissue of the bone may include a rod for being rotated, for pushing, via complementary threads, an arm including the at least one projectable element.

The second mechanism for drawing the at least two projectable elements one towards the other after the projection thereof may include:
- a telescopic connection between rods fixed to the at least two projectable elements; and
- means for sliding the rods one relative to the other.

The telescopic connection between the rods preferably is not circular, for not allowing relative rotation therebetween, thereby the first mechanism for projecting prongs of the at least one projectable element operates together on the at least two projectable elements.

The hollowed shaft may include a slit for each of the at least one projectable element, the slit for not allowing the at least one projectable element to rotate in relation to the shaft.

The slit preferably is elongated for allowing the at least one projectable element to slide therealong, thereby allowing to draw two projectable elements one towards the other after projection thereof into a different location on a bone.

In another aspect, the invention is directed to a method for using a bone affixing apparatus, the method including the step of:
- after inserting the bone affixing apparatus into the bone, projecting at least one projectable element out of a shaft of the bone affixing apparatus into a tissue of the bone, thereby eliminating breaching the bone from the outside of the bone.

The method may further include the step of:
- drawing the at least two projectable elements of the at least one projectable element, one towards the other after the projection thereof,
- thereby allowing drawing two fragments of the bone one towards the other.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

BRIEF DESCRIPTION OF THE DRAWINGS

Embodiments, features, aspects and advantages of the invention are described herein in conjunction with the following drawings.

It should be understood that the drawings are not necessarily drawn to scale.

DESCRIPTION OF EMBODIMENTS

The invention will be understood from the following detailed description of embodiments, which are meant to be descriptive and not limiting. For the sake of brevity, some well-known features, methods, systems, procedures, components, circuits, and so on, are not described in detail.

Figure 1:
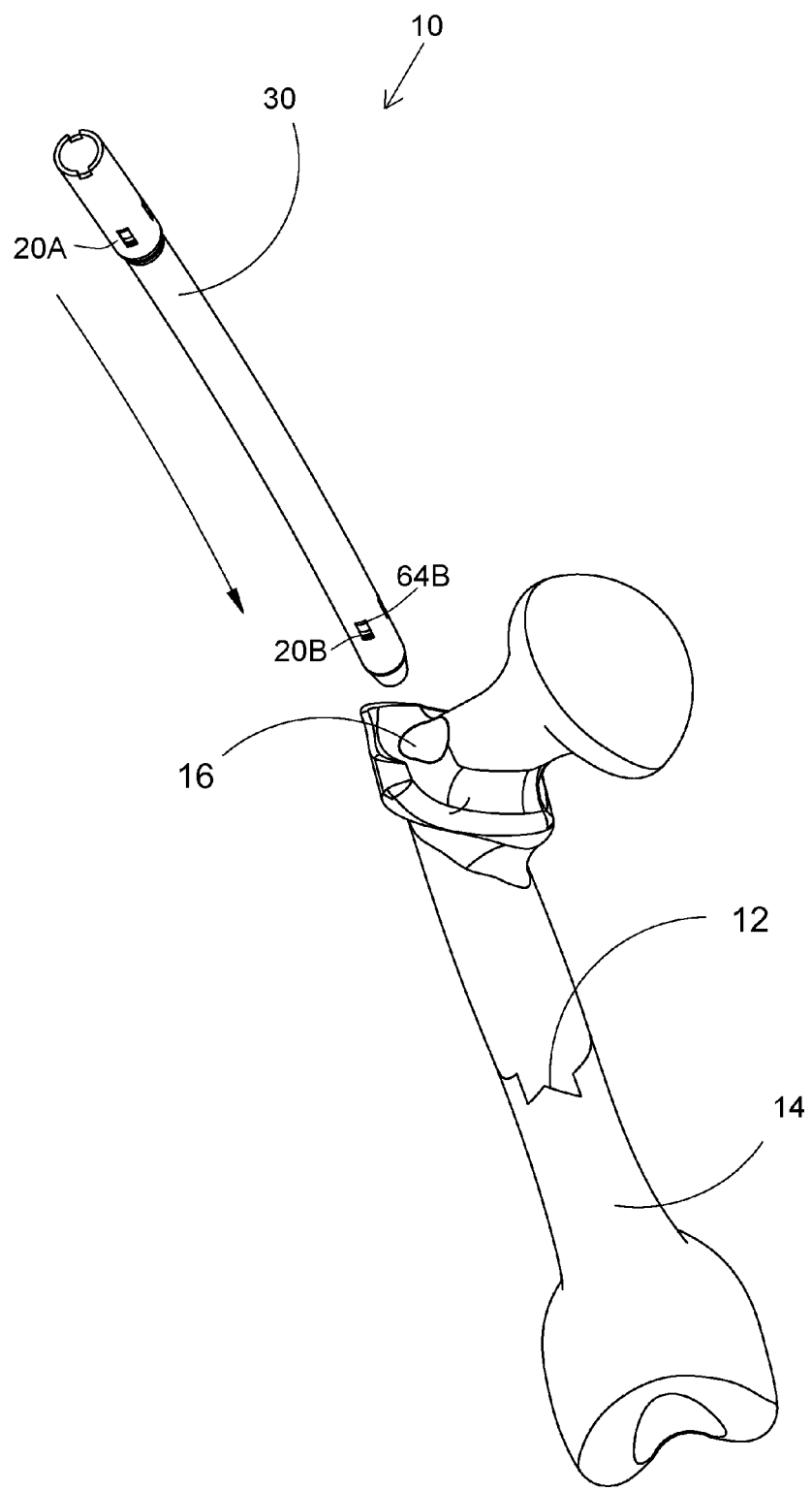
FIG. 1 is a perspective view of a bone affixing apparatus, according to one embodiment of the invention, and a bone to be affixed by the bone affixing apparatus.

FIG. 1 is a perspective view of a bone affixing apparatus, according to one embodiment of the invention, and a bone to be affixed by the bone affixing apparatus.

A bone affixing apparatus 10 includes a hollowed shaft 30 for being inserted into the longitudinal cavity within a bone 14 having a fracture 12. Affixing apparatus 10 further includes projectable elements 20A, 20B, and others, and a mechanism for projecting projectable elements 20A and 20B from hollowed shaft 30 outside towards the tissue 32 (shown in FIG. 2) of bone 14.

At the first step, the doctor drills a hole 16 at one end of bone 14.

Figure 2:
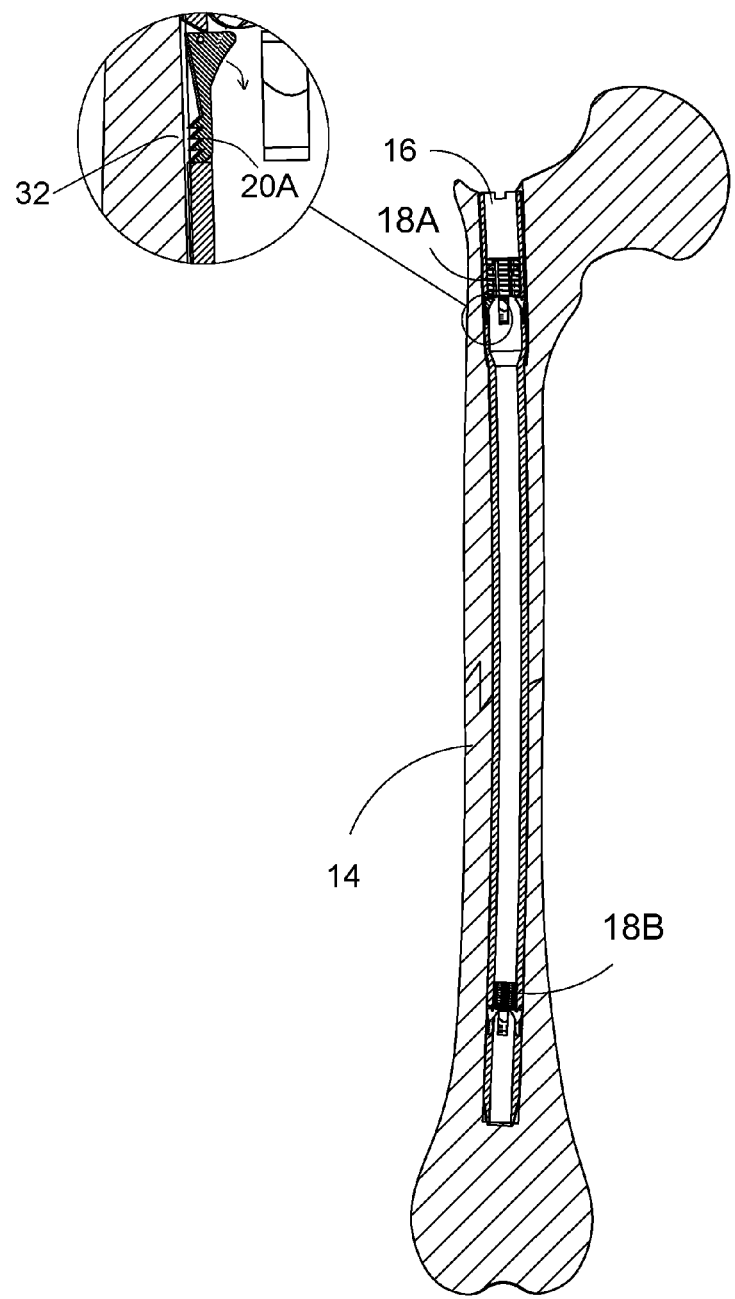
FIG. 2 is a sectional view of the bone affixing apparatus of FIG. 1, inserted into the bone.

FIG. 2 is a sectional view of the bone affixing apparatus of FIG. 1, inserted into the bone.

At the second step, the doctor inserts bone affixing apparatus 10 into the longitudinal cavity through hole 16.

Figure 3:
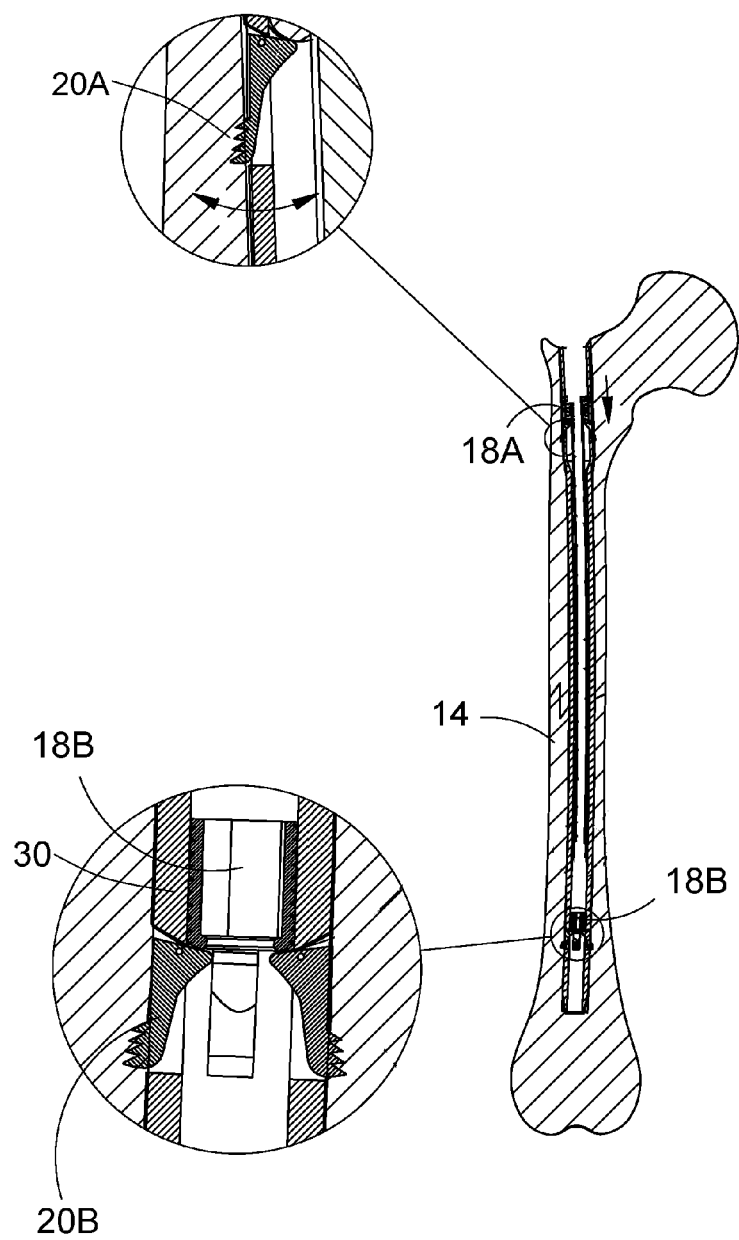
FIG. 3 is a sectional view of the bone affixing apparatus of FIG. 1, wherein the projectable elements of FIG. 1 are projected outside the hollowed shaft.

FIG. 3 is a sectional view of the bone affixing apparatus of FIG. 1, wherein the projectable elements of FIG. 1 are projected outside the hollowed shaft.

At the third step, the doctor projects projectable elements 20A and 20B outside hollowed shaft 30 towards the tissue 32 (shown in FIG. 2) of bone 14, for affixing hollowed shaft 30 to tissue 32 of bone 14.

Figure 4:
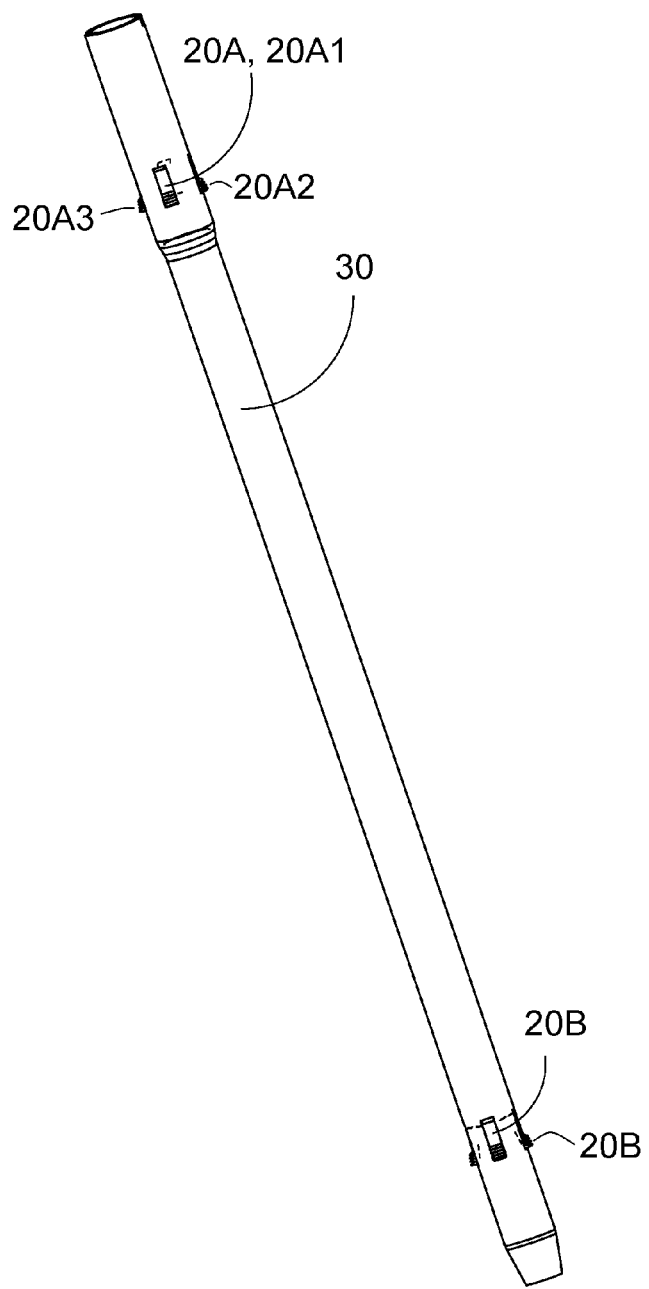
FIG. 4 is a perspective view of the bone affixing apparatus of FIG. 1 alone, at the state of FIG. 3.

FIG. 4 is a perspective view of the bone affixing apparatus of FIG. 1 alone, at the state of FIG. 3.

Projectable elements 20A are preferably located at one end of hollowed shaft 30, and projectable elements 20B are preferably located at the other end of hollowed shaft 30. Additional projectable elements (not shown) may be added along the hollowed shaft, for instance at the middle. Projectable elements 20A at one location include projectable elements 20A1, 20A2, 20A3, etc., each at a different angular position, for being projected at various angular locations.

Figure 5:
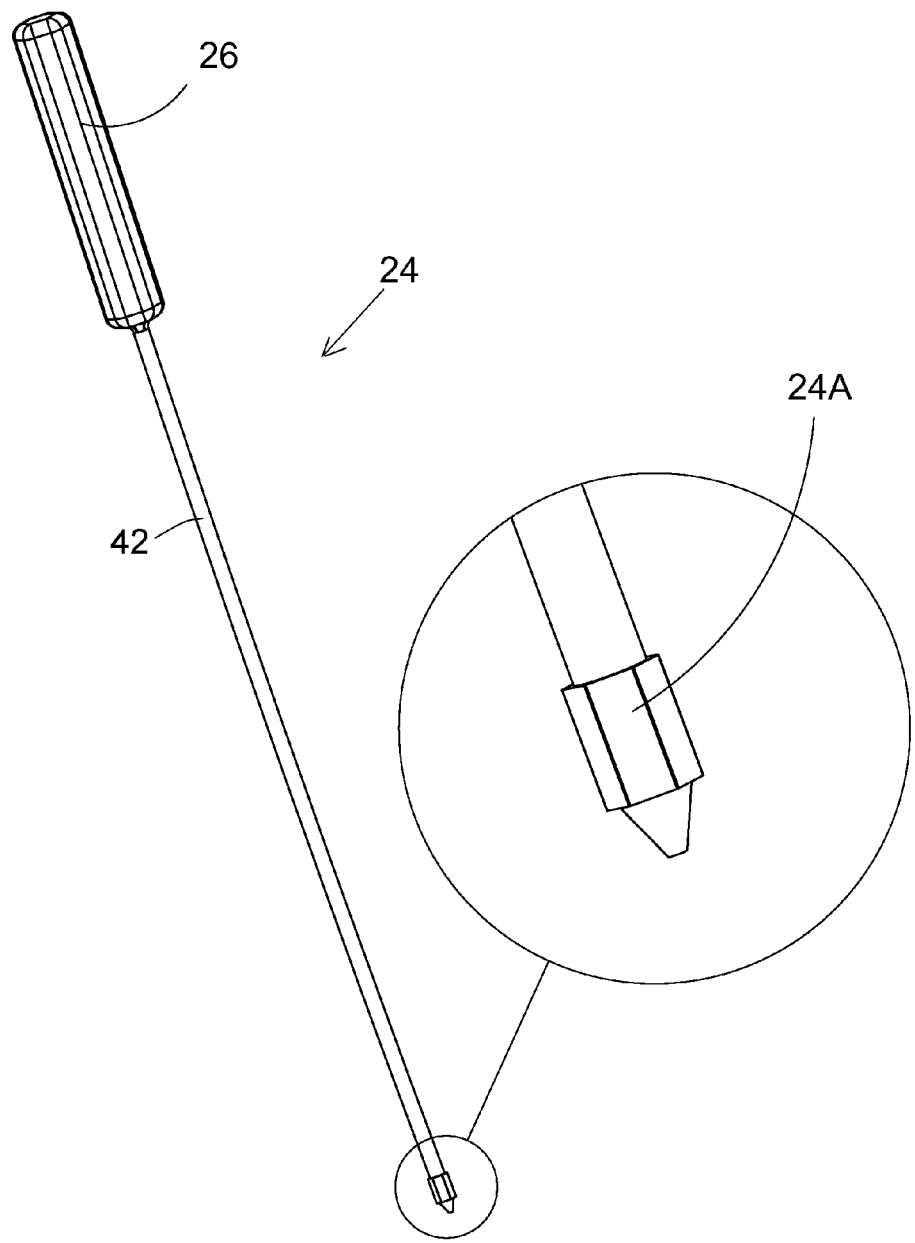
FIG. 5 depicts a screw driver, for projecting the projectable elements of FIG. 4.

FIG. 5 depicts a screw driver, for projecting the projectable elements of FIG. 4.

The projecting of projectable elements 20A and 20B utilizes a projecting mechanism. According to one embodiment, the projecting mechanism includes a screw driver 24, having a handle 26, a rod 42, and a screwing end 24A disposed at the end of rod 42.

Figure 6:
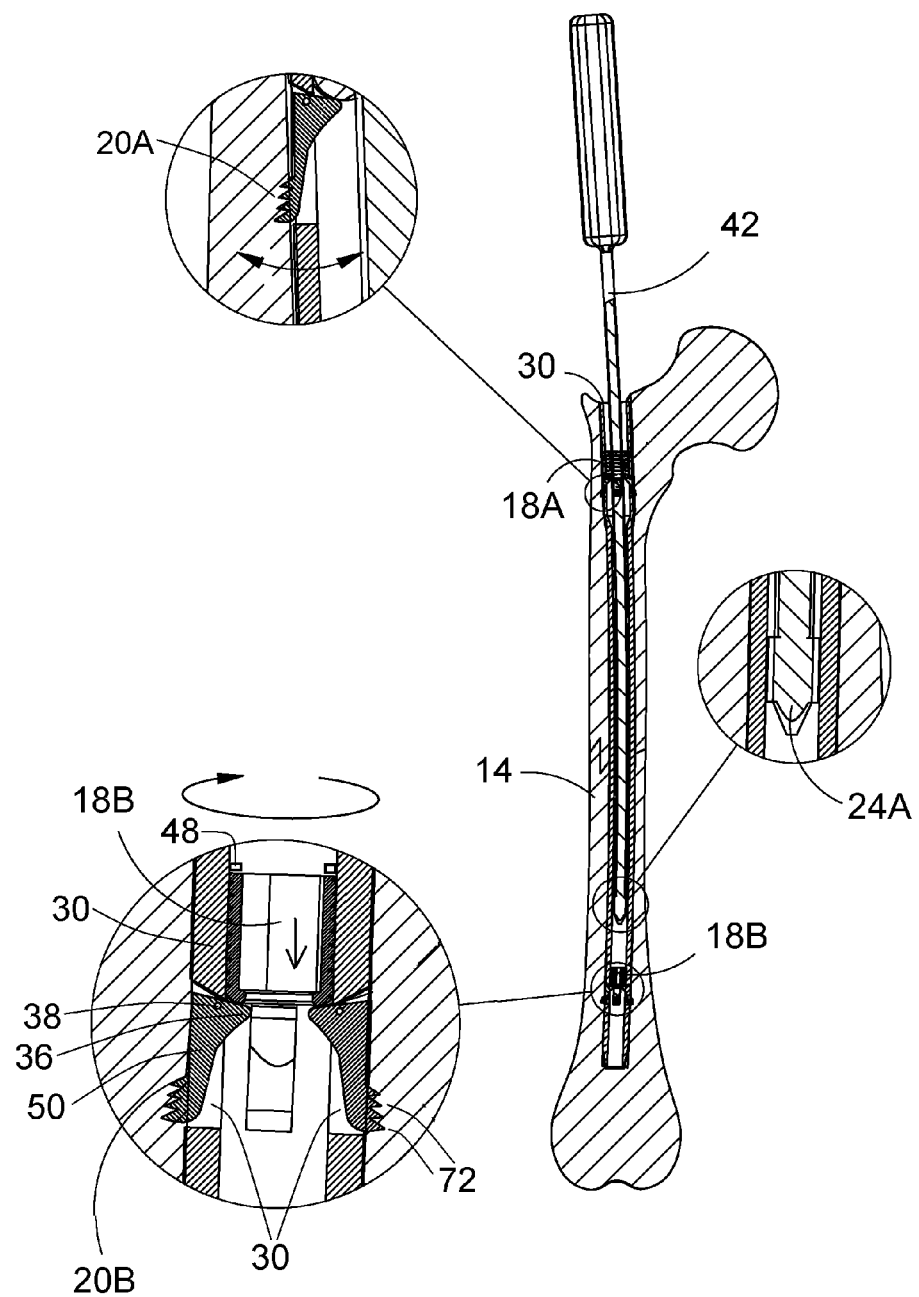
FIG. 6 is the sectional view of the bone affixing apparatus of FIG. 3, into which the screw driver of FIG. 5 is inserted.

FIG. 6 is the sectional view of the bone affixing apparatus of FIG. 3, into which the screw driver of FIG. 5 is inserted.

The doctor may insert rod 42 of screw driver 24 into the longitudinal cavity of hollowed shaft 30 for rotating nuts 18A and 18B disposed within hollowed shaft 30.

Nuts 18A and 18B are rotatable in relation to shaft 30. The outer surface of each of nuts 18A and 18B constitutes a thread 22. Shaft 30 has a thread there, being complementary to thread 22. Thus, the rotation of nut 18B lowers nut 18B The doctor may insert male end 24A, such as an Allen end, of screw driver 24 into a female member of nut 18B for rotating thereof. The lowering of nut 18B pushes a margin 36 of a lever 50. Lever 50 is pivotally connected to hollowed shaft 30 via a pivot 38, and thus the lowering of margin 36 of lever 50 presses prongs 72 of projectable elements 20B of lever 50 outside hollowed shaft 30.

The doctor may then, or before, insert male end 24A of screw driver 24 into a female member of another nut 18A and rotate nut 18A, for pressing projectable elements 20A thereof outside hollowed shaft 30. The doctor may then insert male end 24A of screw driver 24 into a female member of another nut (not shown).

Figure 7:
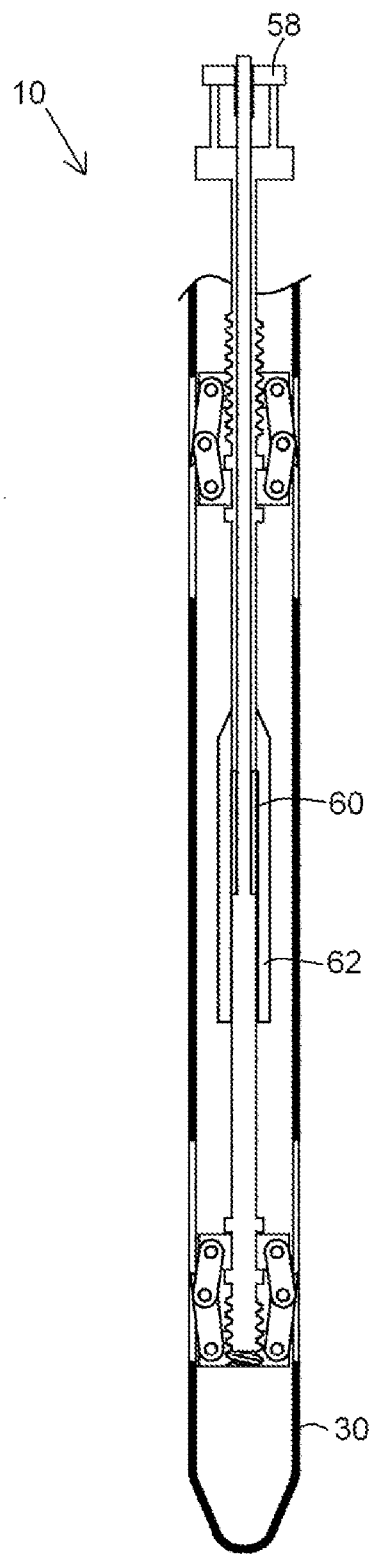
FIG. 7 depicts the bone affixing apparatus according to another embodiment.

FIG. 7 depicts the bone affixing apparatus according to another embodiment.

Figure 8:
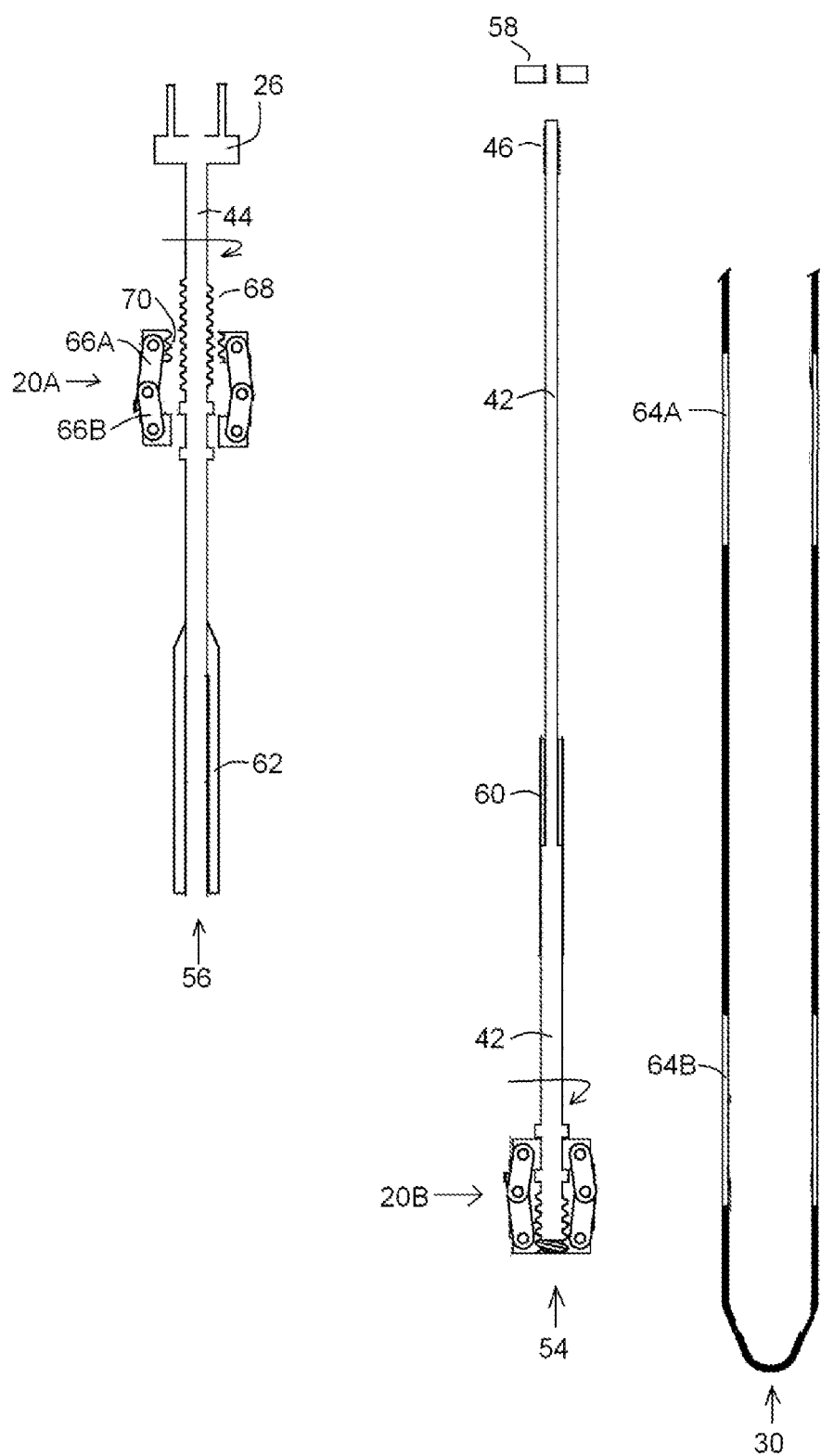
FIG. 8 depicts the parts constituting the bone affixing apparatus of FIG. 7.

FIG. 8 depicts the parts constituting the bone affixing apparatus of FIG. 7.

According to this embodiment, bone affixing apparatus 10 includes hollowed shaft 30; a bottom member 54, including projectable elements 20B, inserted into hollowed shaft 30; a top member 56, including projectable elements 20A, inserted into hollowed shaft 30 and into which bottom member 54 is inserted for being telescopically connected thereto; and a nut 58, for attaching a thread 46 of rod 42 of bottom member 54, for connecting bottom member 54 to top member 56, and for determining the linear disposition therebetween.

Figure 9:
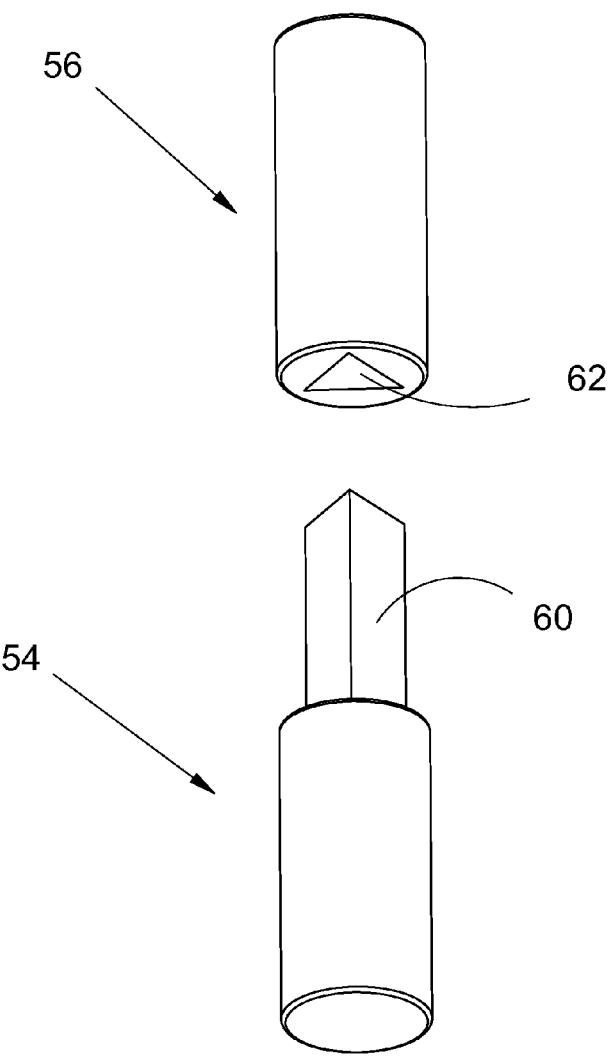
FIG. 9 is a perspective view of the elements joining the bottom member and the top member of FIG. 8.

FIG. 9 is a perspective view of the elements joining the bottom member and the top member of FIG. 8.

Bottom member 54 includes a non-circular male joining element 60; and top member 56 includes a non-circular female joining element 62, being complementary to male joining element 60, for joining therewith. Joining of joining element 60 to joining element 62 prevents rotation of one relative to the other; however, the joining allows linear motion, one relative to the other.

Thus, rotation of handle 26 rotates, except for a rod 44 of top member 56, to which it is fixed, also rod 42 of bottom member 54. This, since bottom member 54 is inserted within top member 56.

Referring again to FIG. 8, projectable elements 20A are disposed facing slits 64A of hollowed shaft 30, and projectable elements 20B are disposed facing slits 64B of hollowed shaft 30. Slits 64A and 64B (shown in perspective in FIG. 1) do not allow rotation of projectable elements 20A and 20B respectively, about hollowed shaft 30.

Thus, rotation of handle 26 rotates rod 44 relative to projectable elements 20A, together with rod 42 relative to projectable elements 20B.

Projectable element 20A is shown in FIG. 8 in an exploded manner. Projectable element 20A includes an arm 66A having a thread 70, for moving against a thread 68 of rod 44; and an arm 66B for maintaining a stationary position in relation to rod 44. Thus, rotation of rod 44, applied by handle 26, folds arms 66A in relation to arm 66B. Projectable element 20B is operated similarly.

Figure 10:
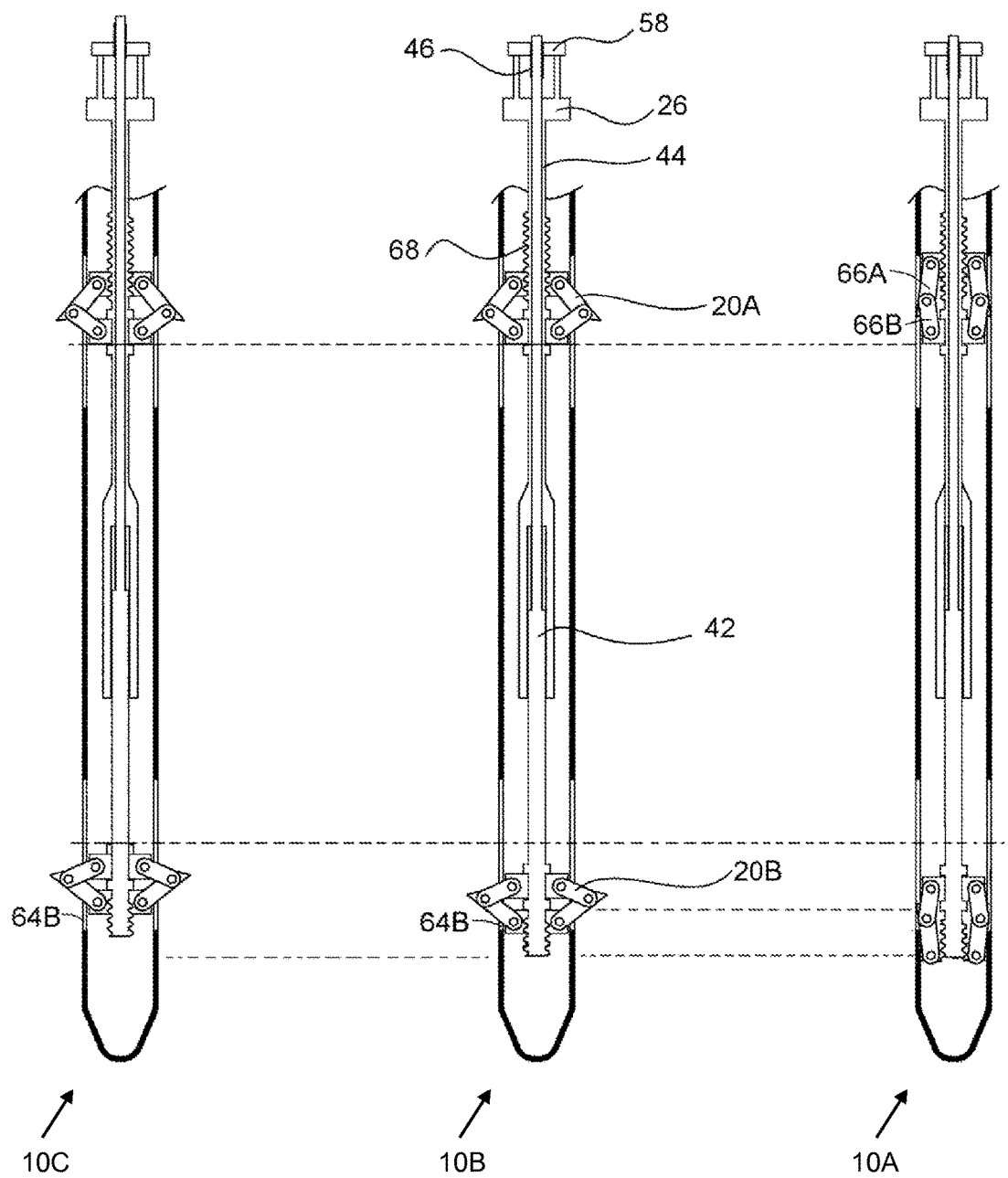
FIG. 10 depicts the steps of operation using the bone affixing apparatus of FIG. 7.

FIG. 10 depicts the steps of operation using the bone affixing apparatus of FIG. 7.

As shown in FIG. 1, at the first step, the doctor drills a hole 16 at one end of bone 14.

Reference numeral 10A of FIG. 10 depicts bone affixing apparatus 10 after the second step.

At the second step, the doctor inserts shaft 30 of bone affixing apparatus 10 into the longitudinal cavity of bone 14. At this state, arms 66A and 66B are not yet folded in relation to one another.

Reference numeral 10B of FIG. 10 depicts bone affixing apparatus 10 after the third step.

At the third step, the doctor rotates handle 26, for rotating rods 42 and 44 together, for projecting projectable elements 20A out of rod 44 and 20B out of rod 42.

Figure 11:
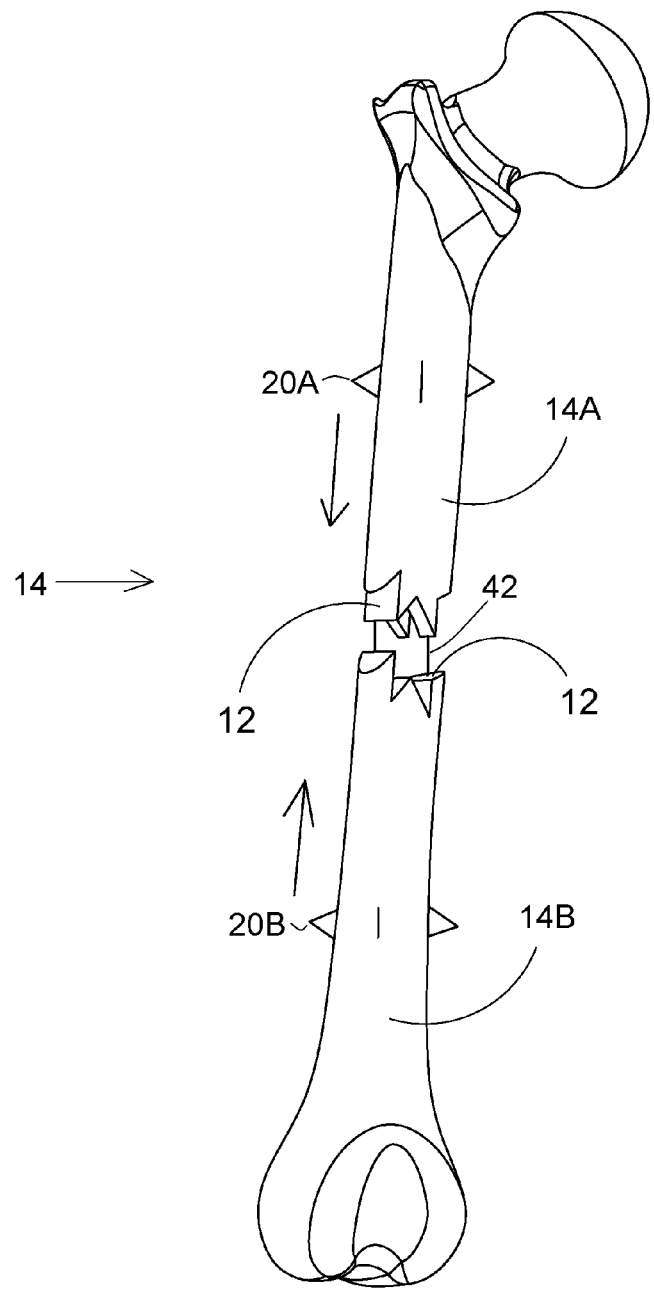
FIG. 11 depicts the bone affixing apparatus of reference numeral 10A of FIG. 10, within the bone, after the third step.

FIG. 11 depicts the bone affixing apparatus of reference numeral 10B of FIG. 10, within the bone, after the third step.

Bone 14 is shown broken into two fragments 14A and 14B. Projectable elements 20A project into fragment 14A and projectable elements 20B project into fragment 14B. However, there is an undesired gap between fragments 14A and 14B, illustrated by rod 42 disposed therebetween. The mechanism for canceling the gap constitutes the telescopic connection of rod 42 to rod 44, and nut 58, for sliding rod 42 relative to rod 44.

Reference numeral 10C of FIG. 10 depicts bone affixing apparatus 10 after the fourth step.

At the fourth step, while not allowing rotating handle 26, rod 42 and rod 44, the doctor rotates screw 58 in relation to handle 26, for linearly sliding rod 42 and projectable elements 20B thereof in relation to rod 44 and projectable elements 20A thereof, for drawing them one towards the other, thereby compressing the entire bone.

Slits 64A and 64B are elongated, for allowing projectable elements 20A and 20B respectively to slide therealong. For example, as reference numeral 10A of FIG. 10 shows, prior to the fourth step, projectable element 64B disposed at the bottom of slit 64B, whereas reference numeral 10B of FIG. 10 shows, after the fourth step, projectable element 64B disposed higher above.

In the figures and/or description herein, the following reference numerals (Reference Signs List) have been mentioned:

numeral 10 denotes a bone affixing apparatus according to one embodiment of the invention;
numeral 12 denotes a fracture in the bone;
numeral 14 denotes the bone;
numerals 14A and 14B denote parts of the broken bone;
numeral 16 denotes a hole drilled in the bone;
numerals 18A and 18B denotes nuts, for being rotated about a complementary thread, for moving linearly upon the rotation;
numerals 20A, 20A1, 20A2, 20A3 and 20B denote projectable elements;
numeral 22 denotes a thread;
numeral 24 denotes a screw driver (nut driver in the example given in the drawings);
numeral 24A denotes an end of a screw driver;
numeral 26 denotes a handle of a screw driver or a handle of a rod, for projecting the projectable projections;
numeral 30 denotes the shaft of the inventive apparatus;
numeral 32 denotes the tissue of the bone;
numeral 36 denotes a margin of a lever;
numeral 38 denotes a pivot of the lever;
numerals 42 and 44 denote rotatable rods, the rotation for projecting the projectable projections;
numeral 46 denotes a thread;
numeral 50 denotes a lever;
numeral 54 denotes a bottom member, including the bottom projectable projection;
numeral 56 denotes a top member, including the top projectable projection;
numeral 58 denotes a nut for connecting the top member to the bottom member, and for sliding them one towards the other;
numerals 60 and 62 denote male and female joining members, providing the telescopic and non-rotational features between the top member and the bottom member;
numerals 64A and 64B denote slits within the hollowed shaft;
numerals 66A and 66B denote arms being pivotally connected therebetween;
numerals 68 and 70 denote complementary threads for moving one in relation to the other; and
numeral 72 denotes a prong.

The foregoing description and illustrations of the embodiments of the invention has been presented for the purposes of illustration. It is not intended to be exhaustive or to limit the invention to the above description in any form.

Any term that has been defined above and used in the claims, should be interpreted according to this definition.

The reference numbers in the claims are not a part of the claims, but rather used for facilitating the reading thereof. These reference numbers should not be interpreted as limiting the claims in any form.

What is claimed is:

1. A bone affixing apparatus, comprising:
a substantially hollowed shaft, for being inserted into a bone;
at least two projectable elements, each disposed at a different longitudinal location along and within said shaft;
a first mechanism, for projecting prongs of at least one of said at least two projectable elements out of said shaft into a tissue of the bone, by rotating a first threaded element in relation to said shaft; and
a second mechanism, for drawing said at least two projectable elements one towards the other, by rotating a second threaded element in relation to said first threaded element and in relation to said shaft,
thereby rotation of said first threaded element together with said second threaded element in relation to said shaft projects said prongs without drawing said at least two projectable elements one towards the other, and
rotation of said second threaded element in relation to said first threaded element and in relation to said shaft draws said at least two projectable elements one towards the other,
thereby eliminating breaching the bone from an outside of the bone, and
thereby allowing drawing two fragments of the bone one towards the other.

2. A bone affixing apparatus according to claim 1, wherein said at least two projectable elements comprises a lever being pivotally connected to said shaft, thereby linear motion of a margin of said lever presses said prongs.

3. A bone affixing apparatus according to claim 1, wherein said rotation of said first threaded element is for pushing a lever, for projecting said at least one of said two projectable elements.

4. A bone affixing apparatus according to claim 1, wherein said second mechanism for drawing said at least two projectable elements one towards the other after the projection thereof includes: a telescopic connection between rods fixed to said at least two projectable elements; and said second threaded element for sliding said rods one relative to the other.

5. A bone affixing apparatus according to claim 4, wherein said telescopic connection between said rods is not circular, for not allowing relative rotation therebetween, thereby said first mechanism for projecting prongs of said at least one of said two projectable elements operates together on said at least two projectable elements.

6. A bone affixing apparatus according to claim 1, wherein said shaft includes a slit for any of said projectable elements, said slit for not allowing said at least two projectable elements to rotate in relation to said shaft.

7. A bone affixing apparatus according to claim 6, wherein said slit is elongated for allowing said at least two projectable elements to slide therealong, thereby allowing to draw said two projectable elements one towards the other after projection thereof into a different location on a bone.

\* \* \* \* \*